(12) United States Patent
Kim

(10) Patent No.: US 11,109,899 B2
(45) Date of Patent: Sep. 7, 2021

(54) MEDICAL INSERTING APPARATUS

(71) Applicant: KYUNGPOOK NATIONAL UNIVERSITY INDUSTRY-ACADEMIC COOPERATION FOUNDATION, Daegu (KR)

(72) Inventor: Kyoungtae Kim, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 149 days.

(21) Appl. No.: 16/468,442

(22) PCT Filed: Dec. 4, 2017

(86) PCT No.: PCT/KR2017/014050
§ 371 (c)(1),
(2) Date: Jun. 11, 2019

(87) PCT Pub. No.: WO2018/110882
PCT Pub. Date: Jun. 21, 2018

(65) Prior Publication Data
US 2020/0397485 A1 Dec. 24, 2020

(30) Foreign Application Priority Data

Dec. 13, 2016 (KR) .......................... 10-2016-0169966

(51) Int. Cl.
*A61B 17/70* (2006.01)
*A61B 17/00* (2006.01)
*A61C 8/00* (2006.01)

(52) U.S. Cl.
CPC ............ *A61B 17/7082* (2013.01); *A61B 2017/00026* (2013.01); *A61C 8/0089* (2013.01)

(58) Field of Classification Search
CPC ...... A61B 17/70; A61B 17/7082; A61B 17/86
See application file for complete search history.

(56) References Cited

U.S. PATENT DOCUMENTS 7,981,144 B2 * 7/2011 Geist ................. A61B 17/8625
606/300
8,070,785 B2 * 12/2011 Biscup ................ A61B 17/686
606/305

(Continued)

FOREIGN PATENT DOCUMENTS

| KR | 10-2007-011220 A | 11/2007 |
| KR | 10-2012-0057758 A | 6/2012 |
| KR | 10-2015-0024235 A | 3/2015 |

*Primary Examiner* — Christopher J Beccia
(74) *Attorney, Agent, or Firm* — Novick, Kim & Lee, PLLC; Sang Ho Lee; Hyun Woo Shin

(57) ABSTRACT

A medical inserting apparatus includes a screw nail which is inserted into a human body, a driver which inserts the screw nail into the human body, a current generator disposed in the driver to generate a predetermined current, a current meter disposed in the driver to measure the current, and a conductor element disposed in the screw nail and the driver along a lengthwise direction including an exposed portion to outside, wherein the conductor element includes a forward conductor element connected to the current generator to allow the current generated by the current generator to flow into the human body, and a reverse conductor element having one end electrically connected to the forward conductor element and the other end connected to the current generator, and including a variable resistor and the current meter installed to allow the current generated by the current generator to flow to the current meter by current division with resistance of the human body.

10 Claims, 7 Drawing Sheets

(56) References Cited

U.S. PATENT DOCUMENTS

| | | | |
|---|---|---|---|
| 8,348,983 B2 * | 1/2013 | Neubardt | A61B 17/8625 |
| | | | 606/304 |
| 9,737,233 B2 * | 8/2017 | Londot | A61B 5/053 |
| 2005/0059972 A1 | 3/2005 | Biscup | |
| 2011/0060240 A1 * | 3/2011 | Londot | A61B 5/6846 |
| | | | 600/547 |
| 2011/0144702 A1 | 6/2011 | Leroux et al. | |
| 2012/0185001 A1 * | 7/2012 | Nayet | A61B 17/8875 |
| | | | 606/301 |
| 2017/0215758 A1 * | 8/2017 | Schepis | A61N 1/36021 |

\* cited by examiner

MEDICAL INSERTING APPARATUS

TECHNICAL FIELD

The present disclosure relates to a medical inserting apparatus, and particularly, to a medical inserting apparatus for correctly identifying the type of tissue surrounding a screw nail inserted into human body to prevent any damage to the nerve by screw nail insertion.

BACKGROUND ART

Medical inserting apparatuses may be inserted into a human body for operations or treatments. For example, medical inserting apparatuses may include pedicle screw nails that are inserted into the spine or implants that replace teeth, etc. Specifically, patients with severe spinal stenosis first, have a surgery for widening the small spinal canal. It is to relieve the pressure on the nerve compressed for a long time by removing the surrounding bone or joint to widen the space. This is called nerve decompression. After the decompression is performed, each segment becomes unstable, and if left alone, many problems occur in the long-term. Therefore, it is necessary to stabilize the condition of the spine by a spinal fusion. This is a process that fixes adjacent vertebrae using pedicle screw nails and fuses them together through bone grafting.

Recently, treatments or operations related to the spine or teeth have dramatically increased, and many studies are actively being conducted on them. In the case of a conventional medical inserting apparatus related to these studies, the medical inserting apparatus has a current generator and a current meter installed therein to apply the electric current into the human body using, the current generator and measure the amount of current coming back using the current meter to identify the type of tissue surrounding the screw nail inserted into the human body. However, in the case of the conventional medical inserting apparatus (see Korean Patent No. 10-1599603), a conductor element to which the current is applied is made of gold, and the nerve has a higher resistance value than the conductor element, so the applied current does not flow into the nerve, and turns back and moves to the current meter. Consequently, it is impossible to identify the resistance value of the tissue through which the current passed, which makes it difficult to correctly identify the type of tissue.

DISCLOSURE

Technical Problem

To solve this problem, there is a need for a medical inserting apparatus that allows a predetermined fraction of current generated by a current generator to flow to the tissue and correctly identifies the type of tissue into which the current flowed.

The present disclosure is directed to providing a medical inserting apparatus that correctly identifies the type of tissue surrounding the screw nail by increasing the resistance value of the conductor element serving as the path the current flows back to allow a predetermined current to flow into the tissue, thereby preventing the screw nail from damaging the nerve when inserting the screw nail.

The problems to be solved by the present disclosure are not limited to those mentioned above, and these and other problems will be clearly understood from the following description.

Technical Solution

To solve the above-described problem, a medical inserting apparatus according to an embodiment of the present disclosure includes a screw nail which is inserted into a human body, a driver which inserts the screw nail into the human body, a current generator disposed in the driver to generate a predetermined current, a current meter disposed in the driver to measure the current, and a conductor element disposed in the screw nail and the driver along a lengthwise direction including a conductor element which is exposed to outside, wherein the conductor element includes a forward conductor element connected to the current generator to allow the current generated by the current generator to flow into the human body, and a reverse conductor element having one end electrically connected to the forward conductor element and the other end connected to the current generator, and including a variable resistor and the current meter installed to allow the current generated by the current generator to flow to the current meter by current division with resistance of the human body.

To solve the above-described problem, a medical inserting apparatus according to another embodiment of the present disclosure includes a screw nail which is inserted into a human body, a driver which inserts the screw nail into the human body, a current generator disposed outside of the screw nail and the driver to generate a predetermined current, a current meter disposed outside of the screw nail and the driver to measure the current, and a conductor element which goes out of the current generator and enters the current generator through inside of the screw nail and the driver including an exposed portion contacting the human body, wherein the conductor element includes a forward conductor element connected to the current generator to allow the current generated by the current generator to flow into the human body, and a reverse conductor element having one end electrically connected to the forward conductor element and the other end connected to the current generator, and including a variable resistor and the current meter installed to allow the current generated by the current generator to flow to the current meter by current division with resistance of the human body.

Advantageous Effects

According to the present disclosure, there is provided a medical inserting apparatus that correctly identifies the type of tissue surrounding the screw nail by increasing the resistance value of the conductor element serving as the path the current flows back to allow a predetermined current to flow to the tissue, thereby preventing the screw nail from damaging the nerve when inserting the screw nail.

DETAILED DESCRIPTION OF MAIN ELEMENTS

Figure 1:
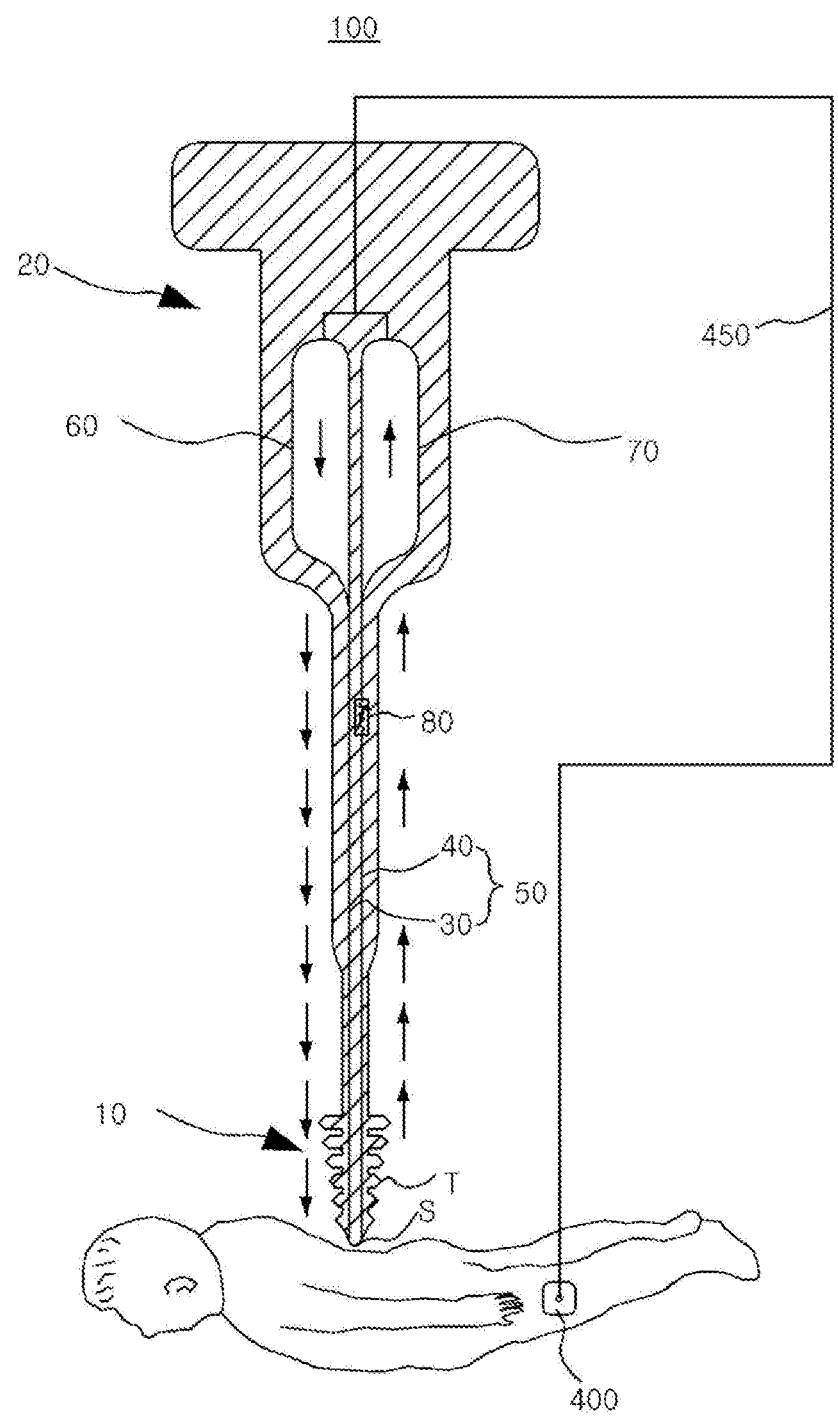
FIG. 1 is a cross-sectional view of a medical inserting apparatus according to an embodiment of the present disclosure.

- 10, 100: Screw nail
- 20, 120, 210: Driver
- 30: Forward conductor element
- 40: Reverse conductor element
- 50, 150, 240: Conductor element
- 60, 160, 250: Current generator
- 70, 170, 260: Current meter
- 80, 180, 270: Variable resistor
- 100, 200, 300: Medical inserting apparatus
- 130, 220: First conductor element
- 135, 225: Third conductor element
- 140: Second conductor element
- 145: Fourth conductor element
- 230: Fifth conductor element
- 235: Sixth conductor element
- 280: External current generation device
- 400: Ground element
- 450: Return element

BEST MODE

These advantages and features of the present disclosure and methods for achieving them will be apparent by referring to the embodiments described in detail below together with the accompanying drawings. However, the present disclosure is not limited to the following disclosed embodiments and will be embodied in many different forms, and these embodiments are only provided to make the disclosure complete and help those having ordinary skill in the technical field pertaining to the present disclosure to understand the scope of the invention fully, and the present disclosure is only defined by the scope of the appended claims. Like reference numerals indicate like elements throughout the specification.

The terminology used herein is only for the purpose of describing the embodiments and is not intended to be limiting of the present disclosure. As used herein, the singular forms are intended to include the plural forms as well, unless the context clearly indicates otherwise. The term "comprises" and/or "comprising" when used in this specification specifies the presence of stated elements, steps and operations, but does not preclude the presence or addition of one or more other elements, steps and operations.

Figure 2:
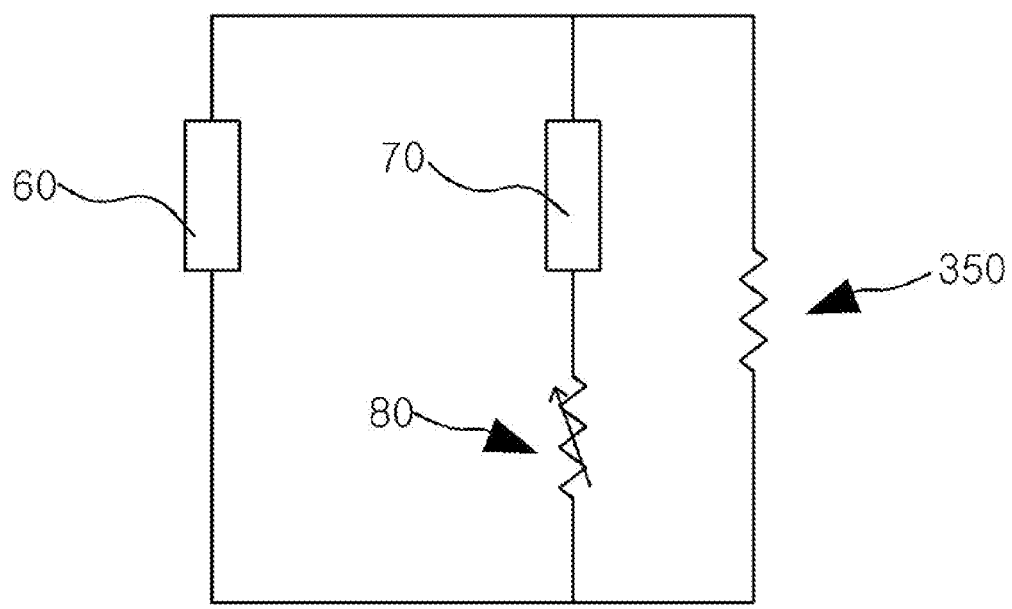
FIG. 2 is a circuit diagram formed by a current generator of a medical inserting apparatus according to an embodiment of the present disclosure and human body.
Figure 3A:
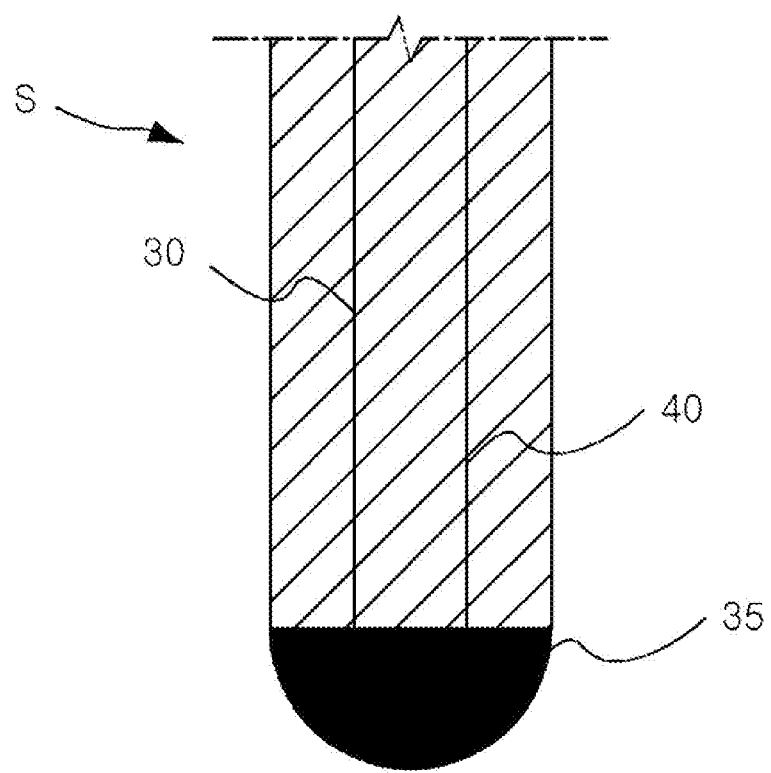
FIGS. 3A and 3B are enlarged views of an exposed portion of a medical inserting apparatus according to the present disclosure.
Figure 3B:
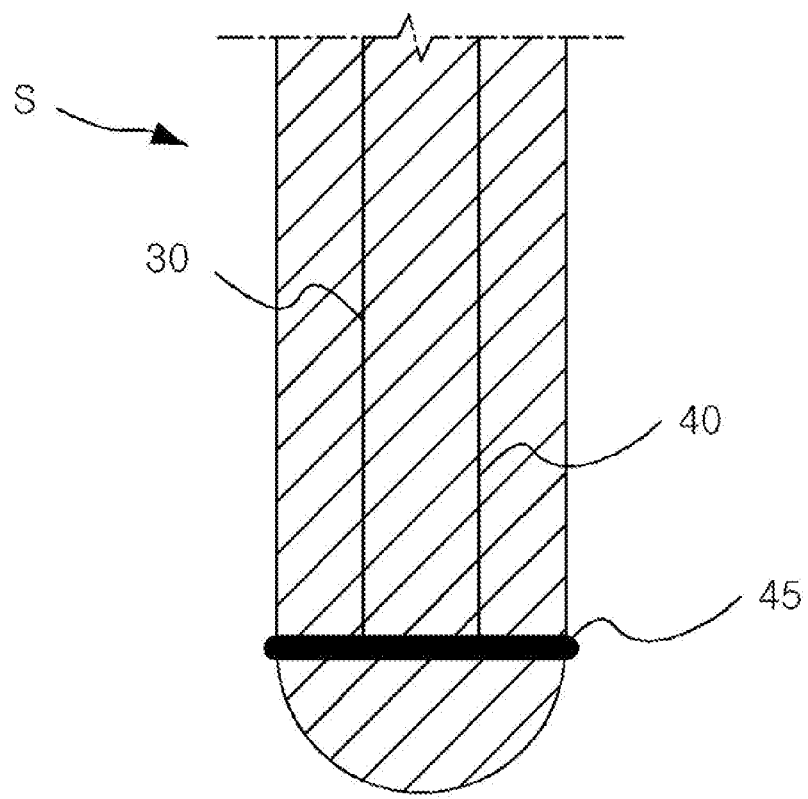

A medical inserting apparatus according to an embodiment of the present disclosure is described with reference to FIGS. 1 to 3. FIG. 1 is a cross-sectional view of the medical inserting apparatus according to an embodiment of the present disclosure. FIG. 2 is a circuit diagram formed by a current generator of the medical inserting apparatus according to an embodiment of the present disclosure and human body. FIGS. 3A and 3B are enlarged views of an exposed portion of the medical inserting apparatus according to the present disclosure.

Referring to FIGS. 1 to 3, the medical inserting apparatus 100 according to an embodiment of the present disclosure includes a screw nail 10, a driver 20, a current generator 60, a current meter 70, a conductor element 50 and a variable resistor 80. Meanwhile, to help an understanding of the present disclosure, the medical inserting apparatus is exaggerated and depicted in a larger size than the human body on the drawings.

The screw nail 10 may be a bone fusion screw nail 10 that is inserted into a tissue 350 of the bone near the nerve, in particular, a pedicle screw nail 10 that is inserted into the spine. The screw nail 10 may have a thread on the outer side for insertion into the human body. Additionally, because the screw nail 10 is inserted into the human body, the screw nail 10 may be made of titanium used as a material for various types of implants because of good biocompatibility and strength.

The screw nail 10 may have a tapping screw T at the front end, and the tapping screw T performs a drilling operation in advance before insertion of the screw nail 10 into the human body, so that the screw nail 10 can be inserted more safely through a hole formed by the tapping screw T.

The driver 20 is an element that inserts the screw nail 10 into the human body or removes the inserted screw nail 10 from the human body, and in the case of the medical inserting apparatus 100 according to an embodiment of the present disclosure, the screw nail 10 and the driver 20 are integrally formed, and as the driver 20 rotates, the screw nail 10 formed integrally with the driver 20 also rotates in the clockwise or counterclockwise direction so that the screw nail 10 may be inserted into the human body or removed from the human body.

The current generator 60 is an element that may be disposed in the driver 20, and generates the current flowing into the human body through the conductor element.

The current meter 70 is an element that may be disposed in the driver 20, and measures the amount of current flowing to the current meter (i.e., the amount of current not flowing into the human body) in the current generated from the current generator 60 by current division with the human body's resistance. The current from the current generator 60 is applied to the human body, and subsequently, a fraction of the current flows into the human body and the remaining current returns to the current meter 70, and thus the amount of current flowing into the human body may be determined by measuring the amount of current returning to the current meter 70, and accordingly the resistance value of the tissue 350 in the human body into which the current flowed may be calculated. It is possible to identify whether the tissue 350 into which the current flowed is a nerve or a muscle by comparing the calculated resistance value and the already known inherent resistance value based on the type of tissue 350.

Meanwhile, the current flowing into the human body goes out through a ground element 400 mounted on a specific part of the human body such as a leg, then returns to the current generator 60 through a return element 450 connected to the ground element 400, and accordingly the medical inserting apparatus 100 according to the present disclosure may form a closed circuit (see FIG. 2). Additionally, the return element 450 may be made of platinum, gold, silver and tungsten, and the material is not limited to a particular type and may include any material that is accepted as suitable for the human body and has very good electrical conductivity.

The conductor element 50 includes an exposed portion S that is disposed in the screw nail 10 and the driver 20 along the lengthwise direction and is exposed to the outside, and when the current generated by the current generator 60 is allowed to flow into the tissue 350 in the human body through the exposed portion S, it is possible to identify the type of tissue 350 disposed surrounding the inserted screw nail 10, thereby preventing the screw nail 10 from contacting the nerve in the process of inserting the screw nail 10.

To this end, the conductor element 50 may include a forward conductor element 30 connected to the current generator 60 to allow the current generated by the current generator 60 to flow into the human body, and a reverse conductor element 40 having one end electrically connected to the forward conductor element 30 and the other end connected to the current generator 60 (to form a closed circuit), and including the variable resistor and the current meter installed to allow the current generated by the current generator to flow to the current meter by current division with the human body's resistance.

That is, the current generator 60, the forward conductor element 30, the reverse conductor element 40 and the current meter 70 form a closed circuit, and a fraction of the current generated by the current generator 60 flows into the tissue 350 in the human body through the forward conductor element 30, and the remaining current passes through the current meter 70 via the reverse conductor element 40, then flows to the current generator 60. Accordingly, it is possible to identify whether the tissue 350 into which the current flowed is a nerve or a muscle by determining a reduced amount of current or the resistance value of the tissue 350 into which the current flowed.

Describing the exposed portion S of the conductor element 50 with reference to FIGS. 3A and 3B, the exposed portion S may be formed by direct connection of the forward conductor element 30 and the reverse conductor element 40, and disposed at the outer periphery of the front end of the screw nail 10. That is, the exposed portion S may include a contact region between the forward conductor element 30 and the reverse conductor element 40 and its surrounding region, and may be attached to the outer periphery of the front end of the screw nail 10.

Alternatively, the exposed portion S may form the outer surface of the front end of the screw nail 10, and be connected to the forward conductor element 30 and the reverse conductor element 40 (see FIG. 3A). In this case, the exposed portion S may be a separate conductor body 35 from the forward conductor element 30 and the reverse conductor element 40, and the conductor body 35 may be attached to the front end of the screw nail 10 and connected to the forward conductor element 30 and the reverse conductor element 40. With the conductor body 35, the contact area of the conductor element 50 with the nerve may increase, which makes it possible to sense the nerve more easily.

Alternatively, the exposed portion S may be in the shape of a ring around the periphery of the front end of the screw nail 10, and be connected to the forward conductor element 30 and the reverse conductor element 40 (see FIG. 3B). The ring-shaped conductor element 45 may run around the periphery of the screw nail 10 at a location that is a predetermined distance apart from the front end of the screw nail 10, and two or more ring shaped conductor elements 45 may be provided.

Meanwhile, the conductor element 50 may be made of platinum, gold, silver and tungsten, and the material is not limited to a particular type and may include any material that is accepted as suitable for a human body and has very good electrical conductivity and is suitable to detect a small electromyogram (EMG) signal.

The variable resistor 80 may be used to correctly identify the type of tissue 350 into which the current flowed. In relation to this, in the case of the conventional medical inserting apparatus, because the resistance value of the nerve is higher than that of the conductor element 50 made of gold, the applied current does not flow to the nerve and turns back and moves to the current meter 70. Accordingly, it is impossible to identify the resistance value of the tissue 350 into which the current flowed, which makes it difficult to correctly identify the type of tissue 350.

To solve this problem, the present disclosure installs the variable resistor 80 to increase the resistance value of the conductor element 50, and as a result, allows a predetermined current to flow to the tissue 350, thereby correctly identifying the type of tissue 350. Moreover, the resistance value of the variable resistor 80 may be automatically or manually adjusted, and the medical inserting apparatus according to the present disclosure may further include a controller to automatically control the variable resistor 80. The controller may be integrally formed with other elements and may be separately formed from other elements, and its installation is not limited to a particular type.

In detail, the variable resistor 80 is equipped in the reverse conductor element 40 at which the current meter 70 is installed, so that the resistance value of the variable resistor 80 may be automatically or manually adjusted to increase the total resistance value of the reverse conductor element 40, and as a consequence, to allow the current generated by the current generator 60 to flow to the tissue 350 in a human body including the nerve. Subsequently, the resistance value of the tissue 350 into which the current flowed may be calculated through the amount of current returning to the current meter 70 (or the amount of current flowing to the tissue 350) and the resistance value of the variable resistor 80, and the type of tissue 350 into which the current flowed may be easily identified by comparing the calculated resistance value and the inherent resistance value of the tissue 350.

Figure 6:
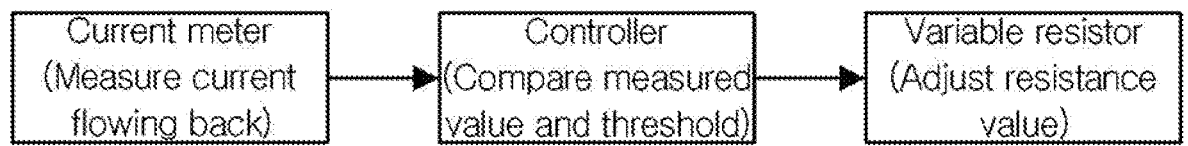
FIG. 6 is a conceptual diagram showing a process of adjusting a resistance value of a variable resistor of a medical inserting apparatus according to the present disclosure.

Meanwhile, describing a process in which the controller adjusts the resistance value of the variable resistor 80 through FIG. 6, the current meter 70 may measure the amount of current flowing back, and transmit the measured value to the controller. Subsequently, the controller may calculate the amount of current flowing into the human body through the received amount of current flowing back, and compare the calculated amount of current with a preset threshold, and when the amount of current flowing into the human body is determined to be less than the threshold, may automatically adjust the resistance value of the variable resistor to allow the current equal to or more than the threshold to flow into a human body.

Further, in the case of the present disclosure, the resistance value of the variable resistor 80 may be automatically or manually adjusted such that a ratio of the amount of current returning to the current meter 70 to the amount of current generated from the current generator 60 is uniform, irrespective of the type of the tissue 350 of the human body into which the current flowed. For example, the variable resistance value may be adjusted such that the amount of current flowing back is ½ of the amount of generated current. In this case, when the tissue 350 into which the current flows is a nerve and when the tissue 350 into which the current flows is a muscle, the resistance value of the variable resistor 80 differs, and through this resistance value difference, the resistance value of the tissue 350 may be calculated. Subsequently, it is possible to correctly identify whether the tissue 350 into which the current flowed is a nerve or a muscle by comparing the calculated resistance value of the tissue 350 and the already known inherent resistance value based on the type of tissue 350.

As a result, by introducing the variable resistor 80, it is possible to correctly identify the type of the tissue 350 surrounding the inserted screw nail 10, and when inserting the screw nail 10 into the human body, it is possible to sense the contact with the nerve in real time, thereby preventing the nerve damage.

Additionally, the driver 20 may have a display including an indicator window or a lamp and an indicator window. It is possible to visually see a reduction in current through the display. In detail, when the current applied to the forward conductor element 30 by the current generator 60 and the current measured by the current meter 70 are displayed in number on the display, it is possible to easily see if there is a reduction in current. Moreover, when the current measured by the current meter 70 is smaller than the current applied to the forward conductor element 30 by the current generator 60, the lamp may light up to easily see if there is a reduction in current. Alternatively, when the current measured by the current meter 70 is smaller than the current applied to the forward conductor element 30 by the current generator 60, an alarm may be set to easily see if there is a reduction in current visually as well as audibly.

Figure 4:
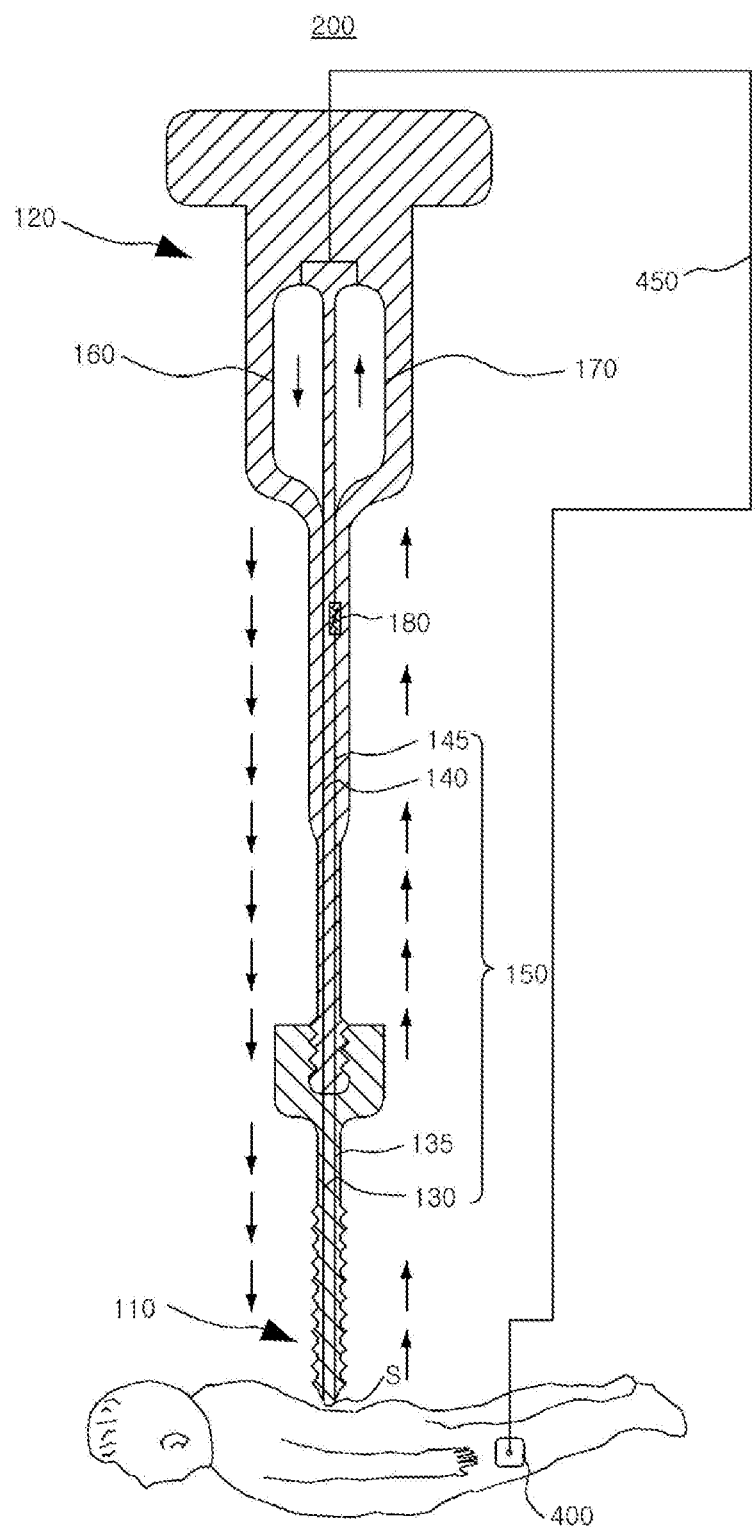
FIG. 4 is a cross-sectional view of a medical inserting apparatus according to another embodiment of the present disclosure.

The medical inserting apparatus according to an embodiment of the present disclosure has been hereinabove described, and a medical inserting apparatus according to another embodiment of the present disclosure will be hereinafter described with reference to FIG. 4. FIG. 4 is a cross-sectional view of the medical inserting apparatus according to another embodiment of the present disclosure.

Referring to FIG. 4, the medical inserting apparatus 200 according to another embodiment of the present disclosure includes a screw nail 110 and a driver 120 that are separate, not integral. For coupling of the screw nail 110 and the driver 120 that are separate components, the screw nail 110 has a coupling groove with a female thread at the head, and the driver 120 has a male thread corresponding to the female thread of the screw nail 110 at the front end, so the screw nail 110 and the driver 120 may be engaged and coupled to each other. However, the coupling method of the screw nail 110 and the driver 120 is not limited to the above-described method, and various coupling methods may be used.

Additionally, the forward conductor element may include a first conductor element 130 disposed in the screw nail 110 and a second conductor element 140 disposed in the driver 120, and the reverse conductor element may include a third conductor element 135 disposed in the screw nail 110 and a fourth conductor element 145 disposed in the driver 120. Accordingly, the second conductor element 140 may be connected to a current generator 160, and the fourth conductor element 145 may be connected to a current meter 170. Meanwhile, when the screw nail 110 and the driver 120 are engaged with each other, the first conductor element 130 and the second conductor element 140 may be connected to form one forward conductor element, and the third conductor element 135 and the fourth conductor element 145 may be connected to form one reverse conductor element.

A variable resistor 180 is installed on the fourth conductor element 145 connected to the current meter 170 to correctly identify whether the tissue 350 into which the current flows is a nerve or a muscle. Meanwhile, the current flowing into the human body goes out through the ground element 400 mounted on a specific part of the human body such as a leg, then returns to the current generator 160 through the return element 450 connected to the ground element 400, and accordingly the medical inserting apparatus 200 according to the present disclosure may form a closed circuit.

In the case of the exposed portion S, similar to the above-described medical inserting apparatus 100 according to an embodiment of the present disclosure, the exposed portion S may be formed by direct connection of the first conductor element 130 and the third conductor element 135, or using a separate conductor body and a ring-shaped conductor.

Figure 5:
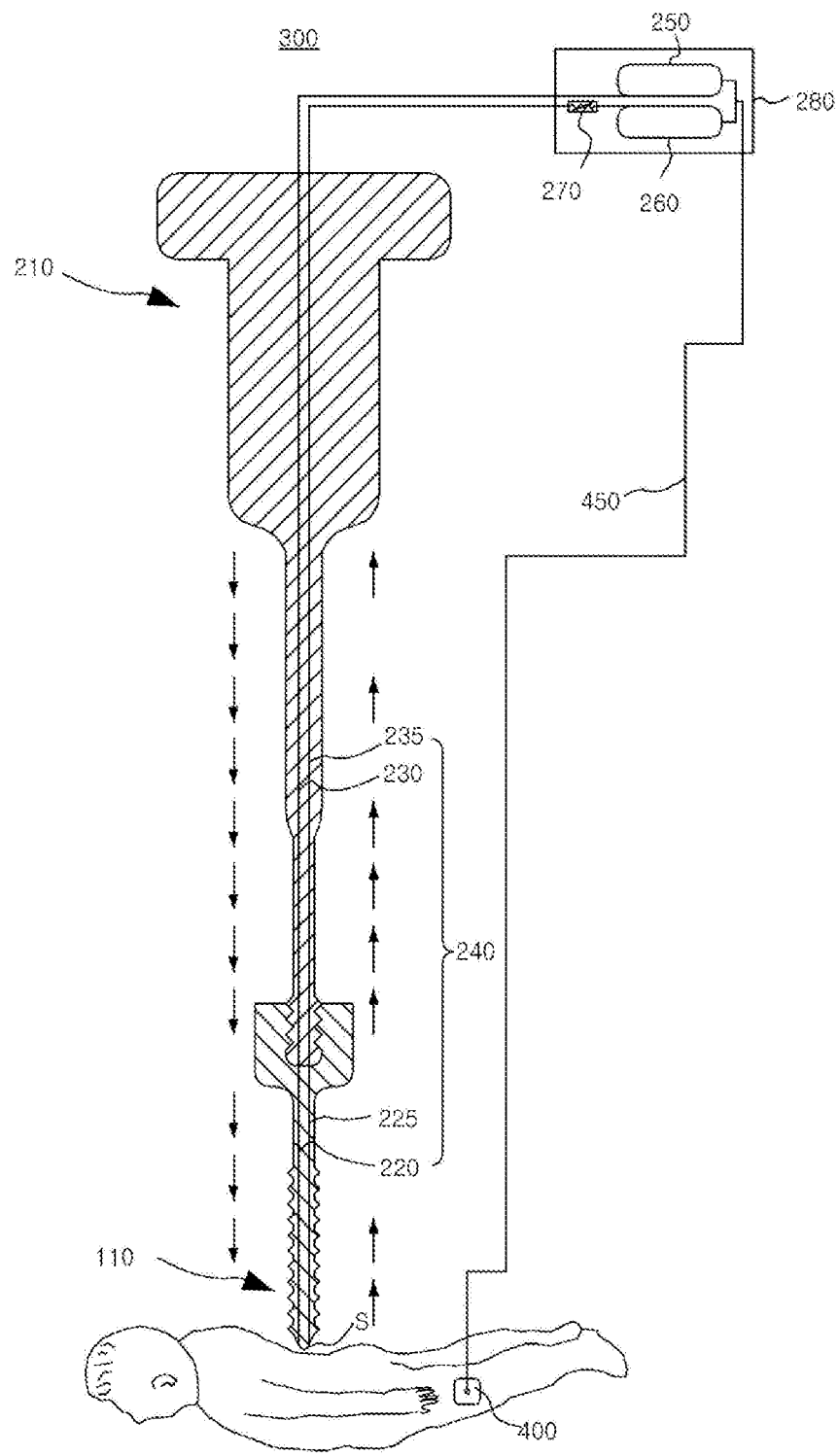
FIG. 5 is a cross-sectional view of a medical inserting apparatus according to still another embodiment of the present disclosure.

The medical inserting apparatus according to another embodiment of the present disclosure has been hereinabove described, and a medical inserting apparatus according to still another embodiment of the present disclosure will be hereinafter described with reference to FIG. 5. FIG. 5 is a cross-sectional view of the medical inserting apparatus according to still another embodiment of the present disclosure.

Referring to FIG. 5, the medical inserting apparatus 300 according to still another embodiment of the present disclosure includes a current generator, a current meter and a variable resistor that are not installed in a driver 210, and instead, are separately provided outside of the driver 210. In detail, the medical inserting apparatus 300 according to still another embodiment of the present disclosure includes an external current generation device 280 including a current generator 250 to generate a current flowing to a conductor element, a current meter 260 to measure the amount of current going back through the human body after generated by the current generator 250, and a variable resistor 270 installed on the path of the current returning to the current meter 260. Because the current generator 250 and the current meter 260 are disposed outside, it is easy to maintain and repair the current generator 250 and the current meter 260.

Additionally, the forward conductor element includes a first conductor element 220 disposed in the screw nail 110 and a fifth conductor element 230 extending outward from the inside of the driver 210 and connected to the current generator, the reverse conductor element includes a third conductor element 225 disposed in the screw nail 110 and a sixth conductor element 235 extending outward from the inside of the driver 210 and connected to the current meter 260, and the variable resistor 270 may be installed on the sixth conductor element 235 in the external current generation device 280. Of course, in some cases, the variable resistor 270 may be installed on the sixth conductor element 235, rather than inside of the external current generation device 280.

Further, the screw nail 110 and the driver 210 may be separate, not integral, and when the screw nail 110 and the driver 210 are engaged with each other, the first conductor element 220 and the fifth conductor element 230 may be connected to form one forward conductor element, and the third conductor element 225 and the sixth conductor element 235 may be connected to form one reverse conductor element.

Meanwhile, although FIG. 5 shows the screw nail 110 and the driver 210 as separate components, as shown in FIG. 1, the screw nail 110 and the driver 210 may be integrally formed, and such an integral medical inserting apparatus may include the external current generation device 280.

Additionally, in the case of the exposed portion S, similar to the above-described medical inserting apparatus, the exposed portion may be formed by direct connection of the first conductor element 220 and the third conductor element 225, or using a separate conductor body and a ring-shaped conductor.

Meanwhile, the current flowing into the human body goes out through the ground element 400 mounted on a specific part of the human body such as a leg, then returns to the current generator 250 through the return element 450 connected to the ground element 400, and accordingly the medical inserting apparatus 300 according to the present disclosure may form a closed circuit.

The invention claimed is:

1. A medical inserting apparatus comprising:
    a screw nail which is configured to be inserted into a human body;
    a driver which is configured to insert the screw nail into the human body, the driver having:
    a current generator generating a predetermined current, and
    a current meter measuring the current; and
    a conductor located within the screw nail and the driver, elongated along a lengthwise direction, and including an exposed portion which is exposed to outside,
    wherein the conductor includes a forward conductor and a reverse conductor, wherein the forward conductor is coupled to the current generator to allow the current generated by the current generator to flow,
    wherein the reverse conductor has one end electrically coupled to the forward conductor and the other end coupled to the current generator, and includes a variable resistor and the current meter installed to allow the current generated by the current generator to flow to the current meter,
    wherein a resistance value of the human body into which the current flowed is calculated through an amount of current measured by the current meter and a resistance value of the variable resistor, and a type of a tissue of the human body is identified by comparing the calculated resistance value and an inherent resistance value of the tissue of the human body, and
    wherein the resistance value of the human body into through the current flowed is calculated by controlling the variable resistor, a ratio of an amount of current returning to the current meter to an amount of current generated from the current generator is managed to be uniform, and the type of the tissue is identified by comparing the calculated resistance value and the inherent resistance value of the tissue.

2. The medical inserting apparatus of claim 1, wherein when, as a result of measurement by the current meter, an amount of current flowing into the human body is determined to be less than a preset threshold, the resistance value of the variable resistor is manually or automatically adjusted to allow the current to be equal to or more than the preset threshold.

3. The medical inserting apparatus of claim 1, wherein the current flowing into the human body goes out through a ground element mounted on the human body, and flows to the current generator through a return element.

4. The medical inserting apparatus of claim 1, wherein the screw nail and the driver are integrally formed.

5. The medical inserting apparatus of claim 4, wherein the screw nail has a tapping screw at a front end thereof.

6. The medical inserting apparatus of claim 1, wherein the screw nail has a coupling groove with a female thread at a head, and the driver has a male thread corresponding to the female thread at a front end thereof, allowing the screw nail and the driver to be engaged with each other.

7. The medical inserting apparatus of claim 6, wherein the forward conductor includes a first conductor disposed in the screw nail and a second conductor disposed in the driver, the reverse conductor includes a third conductor disposed in the screw nail and a fourth conductor disposed in the driver, and when the screw nail and the driver are engaged with each other, the first conductor and the second conductor are coupled to each other, and the third conductor and the fourth conductor are coupled to each other.

8. The medical inserting apparatus of claim 1, wherein the exposed portion is defined by a direct connection of the forward conductor and the reverse conductor, and is disposed on an outer periphery of a front end of the screw nail.

9. The medical inserting apparatus of claim 1, wherein the exposed portion defines an outer surface of a front end of the screw nail, and is coupled to both of the forward conductor and the reverse conductor.

10. The medical inserting apparatus of claim 1, wherein the exposed portion is in a shape of a ring around a periphery of a front end of the screw nail, and is coupled to both of the forward conductor and the reverse conductor.

* * * * *